(12) United States Patent
Becker et al.

(10) Patent No.: US 9,133,321 B2
(45) Date of Patent: Sep. 15, 2015

(54) PENTYL ESTERS OF FURANDICARBOXYLIC ACID AS SOFTENERS

(75) Inventors: Hinnerk Gordon Becker, Essen (DE); Michael Grass, Haltern am See (DE)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

(21) Appl. No.: 14/001,177

(22) PCT Filed: Jan. 27, 2012

(86) PCT No.: PCT/EP2012/051315
§ 371 (c)(1),
(2), (4) Date: Aug. 23, 2013

(87) PCT Pub. No.: WO2012/113608
PCT Pub. Date: Aug. 30, 2012

(65) Prior Publication Data
US 2013/0331491 A1    Dec. 12, 2013

(30) Foreign Application Priority Data
Feb. 24, 2011    (DE) .......................... 10 2011 004 676

(51) Int. Cl.
*C08K 5/1535* (2006.01)
*C07D 307/68* (2006.01)
*C08K 5/00* (2006.01)

(52) U.S. Cl.
CPC ............ *C08K 5/1535* (2013.01); *C07D 307/68* (2013.01); *C08K 5/0016* (2013.01)

(58) Field of Classification Search
None
See application file for complete search history.

(56) References Cited

U.S. PATENT DOCUMENTS

| 8,022,244 | B2 | 9/2011 | Grass et al. |
| 8,258,325 | B2 | 9/2012 | Grass et al. |
| 2007/0060768 | A1 | 3/2007 | Grass et al. |
| 2012/0202725 | A1 | 8/2012 | Grass et al. |
| 2012/0220507 | A1 | 8/2012 | Grass et al. |

FOREIGN PATENT DOCUMENTS

| JP | 2008-127282 A | 6/2008 | |
| WO | WO 2011/023590 A1 | 3/2011 | |
| WO | WO 2011043660 A2 * | 4/2011 | ........... C07D 307/40 |

OTHER PUBLICATIONS

U.S. Appl. No. 14/008,425, filed Sep. 27, 2013, Becker, et al.
U.S. Appl. No. 14/001,597, filed Oct. 8, 2013, Becker, et al.
U.S. Appl. No. 14/001,338, filed Sep. 5, 2013, Becker, et al.
International Search Report issued Mar. 2, 2012 in PCT/EP2012/051315.
P.A. Yoder, et al. "Ueber Dehydroschleimsaure: eine neue Darstellungsmethode, sowie verschiedene Salze und Ester derselben" Berichte Der Deutchen Chemischen, vol. 34, No. 3, XP008148998, Oct. 1, 1901, 17 Pages.
R.D. Sanderson, et al. "Synthesis and Evaluation of Dialkyl Furan-2,5-Dicarboxylates as Plasticizers for PVC" Journal of Applied Polymer Science, vol. 53, No. 13, XP 000464476, Sep. 26, 1994, pp. 1785-1793.

* cited by examiner

*Primary Examiner* — Vu A Nguyen
(74) *Attorney, Agent, or Firm* — Oblon, McClelland, Maier & Neustadt, L.L.P.

(57) ABSTRACT

The invention relates to the use of pentyl esters of furandicarboxylic acid in softeners.

19 Claims, No Drawings

PENTYL ESTERS OF FURANDICARBOXYLIC ACID AS SOFTENERS

This application is a National Stage of PCT/EP12/051315 filed Jan. 27, 2012 and claims the benefit of DE 10 2011 004 676.3 filed Feb. 24, 2011.

The present invention relates to pentyl esters of furandicarboxylic acid.

The invention further provides for the use of these pentyl esters as or in plasticizers and in compositions, especially in those comprising polymers, especially PVC, and a preparation process for these pentyl esters. The invention further provides polymer compositions comprising these pentyl esters and mouldings or films produced from these or using these compositions. Polyvinyl chloride (PVC) is one of the most economically important polymers and is used in various applications both in the form of rigid PVC and in the form of flexible PVC. Important areas of use are, for example, cable sheathing, floor coverings, wallpaper and frames for plastic windows. To increase the elasticity and for better processability, plasticizers are added to the PVC. These customary plasticizers include, for example, phthalic esters such as di-2-ethylhexyl phthalate (DEHP), diisononyl phthalate (DINP) and diisodecyl phthalate (DIDP). Due to their toxicological properties, there are efforts to replace phthalic esters with other plasticizers. Alternative plasticizers which have been described recently are therefore, for example, cyclohexanedicarboxylic esters such as diisononyl cyclohexane carboxylic ester (DINCH).

In addition, the prior art has also described esters of terephthalic acid as alternative plasticizers.

With regard to the raw material basis, the distinctive feature of the present invention lies in the optional use of renewable raw materials to produce the inventive furandicarboxylic esters. In the context of the present invention, renewable raw materials, in contrast to petrochemical raw materials based on fossil resources, for example mineral oil or hard coal, are understood to mean those raw materials which form or are produced on the basis of biomass. The terms "biomass", "biobased" or "based on" and "produced from renewable raw materials" encompass all materials of biological origin which originate from what is called the "short-term carbon cycle" and are thus not part of geological formations or fossil strata. Renewable raw materials are identified and quantified according to ASTM method D6866. One characteristic feature of renewable raw materials is the proportion of the carbon isotope $^{14}C$ therein as contrasted with petrochemical raw materials.

It is known that, with increasing alkyl chain length of the esters, there is a rise in the incompatibility thereof with polymers, especially with PVC. This can have the consequence, for example, that PVC compositions which contain such molecules, for example as plasticizers, exhibit atypical and unforeseeable viscosity profiles which complicate processing. In the production of films, it is often found that they have an increasingly nontransparent appearance, and discoloration of the film occurs, which is reflected, for example, in an increased yellowness which is undesirable in most applications. A lower compatibility of plasticizers and PVC also reduces the permanence of the plasticizer, which means that these plasticizers escape relatively rapidly from the semifinished or finished PVC product, which leads to embrittlement of the product and hence to a significant reduction in the function and value of the corresponding product. The behaviour of the plasticizer is also referred to as "exudation" or "sweating".

Secondly, it is also known that esters with short alkyl chains generally firstly have relatively high volatility, but secondly also, especially where esters with high gelating capacity are concerned, lead when processed in PVC pastes to pastes with low storage stability, the shear viscosity of which frequently depends very greatly on the shear rate, which again leads to restricted processability.

In the production of PVC plastisols, particular care should be taken that a minimum viscosity is maintained in the course of processing in order to achieve homogeneous distribution of the plasticizer in the PVC. Furthermore, high storage stability of the PVC plastisol and low dependence of the shear viscosity of the paste on the shear rate are also desirable. Unfilled films produced from PVC plastisols should be transparent and have minimum yellowness. The plasticizer should additionally have high permanence.

In the prior art, various alternative plasticizers have become known for use in PVC. EP 1 808 457 A1 describes the use of dialkyl terephthalates, which are characterized in that the alkyl radicals have a longest carbon chain of at least 4 carbon atoms and have a total number of carbon atoms per alkyl radical of 5. It is also stated that terephthalic esters having 4 or 5 carbon atoms in the longest carbon chain of the alcohol have good suitability as fast-gelating plasticizers for PVC.

In addition, the use of C5-alkyl esters of citric acid as plasticizers with good gelating properties is also known from EP 1864964B1.

Many of the esters of furandicarboxylic acid are room temperature crystalline solids which, being solids, can be used only with difficulty for the production of liquid compositions, especially of (polymer) plastisols. Thus, the production of polymer passes or plastisols on the industrial scale can be achieved only with liquid plasticizers. Solid plasticizers have to be dissolved beforehand in appropriate solvents, which makes the process inconvenient and costly, and in many applications leads to problems with the material properties as a result of evaporation of the solvents used during the processing.

The technical object of the invention was therefore to provide compounds which can be used as or in plasticizers and which can also be processed in plastisols, have good gelation properties, exhibit low dependence of the plastisol viscosity on the shear rate in plastisols, and have low yellowness and high transparency when processed to give films. It was an additional object to solve the solution to this technical objective in connection with a substance or compound which can be produced at least partly from renewable raw materials.

This technical object is achieved by pentyl esters of furandicarboxylic acid.

These pentyl esters are preferably dipentyl esters.

More particularly, the technical object is achieved by pentyl esters of furandicarboxylic acid which have at least one of the following properties:
  density at 20° C. is not more than 1.06 g/cm$^3$;
  intrinsic viscosity at 25° C. is not more than 60 mPa*s;
  when analyzed with a differential calorimeter, there is no melting signal at temperatures >25° C.

In a further embodiment, the pentyl ester has at least two of the aforementioned properties.

A particular economic and simultaneously environmental advantage of the present invention lies in the simultaneous use of renewable and petrochemical raw materials for the production of the inventive furandicarboxylic esters, which firstly enables particularly inexpensive production and wide usability, but secondly also leads to particularly "sustainable" products.

It has been found that, surprisingly, such pentyl esters, unlike the corresponding homologous butyl and hexyl esters, are not solids and have good processability as liquids at room temperature. The corresponding homologous di-n-butyl furandicarboxylates and di-n-hexyl furandicarboxylates are solid at room temperature and have melting points in the range of 30-40° C. They therefore cannot be used on the industrial scale for production of polymer pastes or plastisols.

Di-n-butyl furandicarboxylate and di-n-hexyl furandicarboxylate are known from the studies of Sanderson et al (R. D. Sanderson, D. F. Schneider, I. Schreuder; J. Appl. Polym. Sci.; 53 (1991): 1785-1793). These are crystalline solids with melting points of approx. 42° C. (di-n-butyl furandicarboxylate) and approx. 32° C. (di-n-hexyl furandicarboxylate), which cannot be used viably for numerous applications, for example the production of polymer pastes.

Dipentyl esters of furandicarboxylic acid have not been described to date; more particularly there are no suggestions to use dipentyl esters of furandicarboxylic acid in polymer compositions and/or as plasticizers.

It has now been found that, surprisingly, the inventive pentyl esters can be produced in liquid form without solidification, and can be used advantageously as a component in polymer formulations, for example as plasticizers in PVC formulations.

It has additionally been found that the inventive pentyl esters have excellent gelation properties when they are processed with PVC. These gelation properties are actually better than the gelation properties of the corresponding dialkyl terephthalates.

The PVC pastes based on the inventive pentyl esters have only a low dependence of the paste viscosity on the shear rate. They are thus processable within a wide shear rate range and with a wide variety of different processing methods.

Due to the favourable gelation characteristics, the corresponding PVC pastes can be processed more rapidly or at lower temperatures.

It has additionally been found that transparent PVC films which comprise the inventive plasticizer have a very high transparency, which is in some cases higher than that of films which have been produced with dibutyl terephthalate as a plasticizer.

In a preferred embodiment, the pentyl ester is a dipentyl furan-2,5-dicarboxylate. This may also be present in the form of at least two isomeric dipentyl furan-2,5-dicarboxylates.

In a preferred embodiment, esters of isomeric dipentyl furan-2,5-dicarboxylates are also used the latter comprising pentyl groups selected from: n-pentyl, 2-pentyl, 3-pentyl, 2-methylbutyl, 3-methylbutyl, 3-methylbut-2-yl, 2-methylbut-2-yl groups.

Particular preference is given to using mixtures of n-pentanol and 2-methylbutanol in a mass ratio of 99.9 to 70% pentanol and 0.1 to 30% 2-methylbutanol.

The alkyl radicals of the furandicarboxylic esters are preferably more than 60% n-pentyl radicals. Preferably, the alkyl radicals of the dialkyl terephthalates are from 70 to 99.9% n-pentyl radicals and from 30 to 0.1% methylbutyl radicals, especially 2-methylbutyl radicals, more preferably from 85 to 98% n-pentyl radicals and from 15 to 2% methylbutyl radicals, especially 2-methylbutyl radicals, and most preferably from 90 to 96% n-pentyl radicals and from 10 to 4% methylbutyl radicals, especially 2-methylbutyl radicals. Preferably, the methylbutyl radicals are more than 50%, preferably more than 75% and more preferably more than 95% 2-methylbutyl radicals. The percentage distribution of the $C_5$-alkyl radicals can be determined in a simple manner by hydrolyzing the esters, removing the alcohol obtained and analyzing the alcohol by gas chromatography (GC). For example, the gas chromatography separation can be performed on a polydimethylsiloxane column (e.g. DB 5) as the stationary phase with a length of 60 m, an internal diameter of 0.25 mm and a film thickness of 0.25 µm.

In a further particular, preferred embodiment, the inventive pentyl ester is a di-n-pentyl ester. This has the advantage that it is a compound with distinct molecular structure which can be produced in an unproblematic manner from the industrially available raw material n-pentanol.

In a further particular, preferred embodiment, at least one of the two ester groups of the inventive pentyl ester is a 2-methylbutyl or 3-methylbutyl group. This has the advantage that the pentyl esters have a particularly high storage stability both intrinsically and in polymer compositions.

In a further preferred embodiment, the inventive pentyl esters are ester mixtures of isomeric pentanols. This has the advantage that it is possible here to produce mixtures with a very low crystallization tendency, which lead to good low-temperature properties in polymer compositions.

The inventive pentyl esters can preferably be prepared using primary alcohols or alcohol mixtures as obtainable, for example, by hydroformylation of an alkene with subsequent hydrogenation. Precursors of pentanols are preferably technical hydrocarbon mixtures which contain one or more olefin(s) having 4 carbon atoms. The most important source for $C_4$-olefins is the $C_4$ cut of cracked gasoline from steamcrackers. This is used to produce, after extraction/extractive distillation of the butadiene or the selective hydrogenation thereof to give an n-butene mixture, a hydrocarbon mixture (raffinate I or hydrogenated crack-$C_4$) which comprises isobutene, 1-butene and the two 2-butenes. Another raw material for $C_4$-olefins is the $C_4$ cut from FCC plants, which can be worked up as described above. $C_4$-Olefins produced by Fischer-Tropsch synthesis are, after selective hydrogenation of the butadiene present therein to give n-butenes, likewise a suitable feedstock. In addition, olefin mixtures which are obtained by dehydrogenating $C_4$ hydrocarbons or by metathesis reactions, or other technical olefin streams may be suitable feedstocks. In addition to raffinate I, suitable precursors for the pentanols are also raffinate II and/or raffinate III, a stream which is obtained by removing the majority of 1-butene from the raffinate II, and what is called crude butane, which is obtained after an oligomerization of raffinate II and which, in addition to alkanes, comprises 2-butene as virtually the exclusive olefin. The advantage of the use of raffinate II, raffinate III or crude butane as a precursor for pentanols is that these precursors contain virtually no isobutene, if any, and the pentanols present therefore contain only small amounts (less than 0.5% by mass in relation to the pentanols), if any, of 3-methylbutanol.

Due to the frequently very high separation complexity for separation of the starting mixtures, it may be advantageous not to separate the olefins present in the technical mixture for use as the starting mixture, but to use the mixtures directly.

In the inventive compositions, further additional plasticizers excluding pentyl esters of furandicarboxylic acid may preferably be present.

Such additional plasticizers are, for example, selected from the following list: dialkyl phthalates, preferably having 4 to 13 carbon atoms in the alkyl chain; trialkyl trimellitates, preferably having 4 to 9 carbon atoms in the side chain; dialkyl adipates, preferably having 4 to 9 carbon atoms in the side chain; dialkyl terephthalates, preferably each having 4 to 13 carbon atoms, especially 4 to 9 carbon atoms, in the side chain; alkyl 1,2-cyclohexanediesters, alkyl 1,3-cyclohexanediesters and alkyl 1,4-cyclohexanediesters, preference being given here to alkyl 1,2-cyclohexanediesters, preferably in each case with 4 to 10 carbon atoms in the side chain; dibenzoic esters of glycols; alkylsulphonic esters of phenol with preferably one alkyl radical containing 8 to 22 carbon atoms; glyceryl esters; isosorbide esters, especially isosorbide diesters; epoxidized vegetable oils; saturated or unsaturated fatty acid esters which may also be partially or fully epoxidized; citric triesters with a free or carboxylated OH group and for example, alkyl radicals of 4 to 8 carbon atoms, alkylpyrrolidone derivatives with alkyl radicals of 4 to 18 carbon atoms and alkyl benzoates, preferably with 7 to 13 carbon atoms in the alkyl chain. In all cases, the alkyl radicals may be linear or branched and identical or different.

More preferably, in the inventive mixtures, no ortho-phthalate is used as additional plasticizer. In a particular embodiment, at least one of the additional plasticizers used in the inventive composition is a trialkyl trimellitate. This trialkyl trimellitate preferably has ester side chains having 4 to 9 carbon atoms, where the ester groups may have either the same or a different number of carbon atoms. More preferably, at least one of the ester groups present is a group having not more than 8 carbon atoms per ester group, especially preferably a group having not more than 7 carbon atoms and most preferably a group having not more than 6 carbon atoms. The combination of the inventive pentyl esters with trialkyl trimellitates, when used in PVC plastisols, leads especially to products which have a low proportion of volatile constituents and good thermal stability.

In a further particular embodiment, at least one of the additional plasticizers used in the inventive composition is a dialkyl adipate. This dialkyl adipate preferably has ester side chains having 4 to 9 carbon atoms, where the ester groups here too may have either the same or a different number of carbon atoms. More preferably, at least one of the ester groups present is a group having not more than 8 carbon atoms per ester group, especially preferably a group having not more than 7 carbon atoms. More particularly, at least one of the dialkyl adipates used is dioctyl adipate. The combination of the inventive dipentyl furandicarboxylates with dialkyl adipates, when used in PVC plastisols, leads especially to products which have a low plastisol viscosity and, in the processed state, good low-temperature properties (for example a very low glass transition temperature).

In a further particular embodiment, at least one of the additional plasticizers used in the inventive composition is a dialkyl terephthalate. This dialkyl terephthalate preferably has ester side chains having 4 to 13 carbon atoms, where the ester groups may again have either the same or a different number of carbon atoms. More preferably, at least one of the ester groups present is a group having not more than 10 carbon atoms per ester group, especially preferably a group having not more than 9 carbon atoms and most preferably a group having not more than 8 carbon atoms. More particularly, at least one of the dialkyl terephthalates used is di(isononyl) terephthalate, di(2-ethylhexyl) terephthalate, di-n-heptyl terephthalate, diisoheptyl terephthalate, di-n-butyl terephthalate, di(3-methylbutyl) terephthalate or di-n-pentyl terephthalate. The combination of the inventive dipentyl furandicarboxylates with dialkyl terephthalates, when used in PVC plastisols, leads especially to products which (according to the ester chain length of the dialkyl terephthalates used) have a very good thermal stability and good low-temperature properties with a simultaneously low level of volatile constituents.

In a further particular embodiment, at least one of the additional plasticizers used in the inventive composition is a dialkyl ester of cyclohexanedicarboxylic acid, more preferably a dialkyl ester of 1,2-cyclohexanedicarboxylic acid. Preferably, this dialkyl cyclohexanedicarboxylate has ester side chains having 4 to 10 carbon atoms, where the ester groups may again either have the same or a different number of carbon atoms. More preferably, at least one of the ester groups present is a group having not more than 9 carbon atoms per ester group, especially preferably a group having not more than 8 carbon atoms and most preferably a group having not more than 7 carbon atoms. More particularly, at least one of the dialkyl cyclohexanedicarboxylates used is di-iso-nonyl 1,2-cyclohexanoate, di-2-ethylhexyl 1,2-cyclohexanoate, di-n-pentyl 1,2-cyclohexanoate, di-n-heptyl 1,2-cyclohexanoate, di-iso-heptyl 1,2-cyclohexanoate, di-n-butyl 1,2-cyclohexanoate, di-n-butyl 1,4-cyclohexanoate, di-n-butyl 1,3-cyclohexanoate or di(3-methylbutyl) 1,2-cyclohexanoate. The combination of the inventive dipentyl furandicarboxylates with dialkyl esters of cyclohexanedicarboxylic acid, when used in PVC plastisols, leads especially to products which have the particular features of very high hydrolysis stability and very low plastisol viscosity with simultaneously good gelation properties.

In a further particular embodiment, at least one of the additional plasticizers used in the inventive composition is a glyceryl ester, more preferably a glyceryl triester. The ester groups may either be of aliphatic or aromatic structure. This glyceryl ester preferably has ester side chains having 1 to 24 carbon atoms, where the ester groups may again have either the same or a different number of carbon atoms. More preferably, one of the ester groups is hydroxystearic acid, where the hydroxyl function is preferably likewise esterified, more preferably by an acetyl to group. Additionally more preferably, at least one of the ester groups present is a group having not more than 9 carbon atoms per ester group, especially preferably a group having not more than 8 carbon atoms and most preferably a group having not more than 7 carbon atoms. More particularly, at least one of the glyceryl esters used is a glyceryl triacetate. The combination of the inventive dipentyl furandicarboxylates with glyceryl esters leads especially to particularly sustainable products which can be produced to a large degree on the basis of renewable raw materials.

In a further particular embodiment, at least one of the additional plasticizers used in the inventive composition is a citric triester with a free or carboxylated OH group. The ester groups here too may be either of aliphatic or aromatic structure. The citric triester is especially preferably a trialkyl citrate with a carboxylated OH group. This trialkyl citrate preferably has ester side chains having 1 to 9 carbon atoms, where the ester groups may again have either the same or a different number of carbon atoms. More preferably, at least one of the ester groups present is a group having not more than 9 carbon atoms per ester group, especially preferably a group having not more than 8 carbon atoms and most preferably a group having not more than 7 carbon atoms. More particularly, at least one of the citric esters used is acetyl tributyl citrate, acetyl tri-n-butyl citrate, acetyl tri-n-pentyl citrate or acetyl tri-iso-heptyl citrate. The combination of the inventive dipentyl furandicarboxylates with citric triesters with a free or carboxylated OH group leads especially to plastisols which have particularly good gelating capacity, especially at low temperatures.

In a preferred embodiment, the mass ratio of additional plasticizers used and pentyl esters of furandicarboxylic acid is between 1:20 and 20:1, preferably between 1:10 and 20:1, more preferably between 1:5 and 20:1 and especially preferably between 1:1 and 15:1.

The inventive pentyl esters or the plasticizers produced therefrom may be present in all possible presentation forms, for example as a liquid, especially as a pumpable liquid (pumpable at room temperature), as a paste, protective composition, plastisol, powder or solid. Especially preferably, they are present in liquid form and especially preferably in the form of a pumpable liquid (pumpable at room temperature).

In addition to the pentyl ester itself, a process for preparation thereof is also Claimed.

Process for preparing an above-described pentyl ester, comprising the process steps of:
a) contacting furandicarboxylic acid and/or at least one furandicarboxylic acid derivative, especially dimethyl furandicarboxylate or furandicarbonyl chloride, with one or more aliphatic alcohols having 5 carbon atoms, and optionally one or more esterification catalysts and/or further substances;
b) heating the reaction mixture described to a temperature of >50° C. and esterifying of transesterifying while removing at least one low molecular weight substance from the reaction mixture, the removal in process step b) preferably being effected thermally.

In an alternative process for preparing an above-described pentyl ester, this process comprises the process steps of:
 a) contacting 5-hydroxymethylfurfural and/or at least one furan derivative with one or more aliphatic alcohols having 5 carbon atoms and at least one catalyst and at least one oxygen-containing component;
 b) adjusting the reaction mixture described to a temperature of >0° C. and conducting an oxidative esterification, the term "oxidative esterification" being understood to mean (any) combination of oxidation and esterification in preferably one process step, especially preferably in one reaction space.

The latter process is preferred here.

The pentyl esters can be prepared by "direct" esterification of the furandicarboxylic acid or by transesterification, for example from the methyl esters of the furandicarboxylic acid.

To prepare the inventive pentyl esters by means of esterification, either furandicarboxylic acid or a reactive derivative, for example the corresponding dichloride, is reacted with one or more aliphatic alcohols having 5 carbon atoms. The esterification preferably proceeds from furandicarboxylic acid and one or more aliphatic alcohols having 5 carbon atoms with the aid of a catalyst.

The esterification of the furandicarboxylic acid with one or more aliphatic alcohols having 5 carbon atoms to give the corresponding pentyl esters can be performed autocatalytically or catalytically, for example with Brønsted or Lewis acids. No matter what kind of catalysis is selected, the result is always a temperature-dependent equilibrium between the acid and alcohol feedstocks and the ester and water products. In order to shift the equilibrium in favour of the ester, it is possible to use an entraining agent, with the aid of which the water of reaction is removed from the mixture. Since the alcohols used for the esterification have a lower boiling point than the furandicarboxylic acid, the reactive derivatives thereof and esters thereof, they are frequently used as an entraining agent which, after removal of water, can be recycled back into the process.

The alcohol used to form the pentyl ester or the isomeric pentanol mixture which serves simultaneously as an entraining agent is used in an excess of preferably 5 to 50% by mass, especially 10 to 30% by mass, of the amount needed to form the ester.

The esterification catalysts used may be acids, e.g. Brønsted acids, for example sulphuric acid, methanesulphonic acid or p-toluenesulphonic acid, or metals or compounds thereof (generally Lewis acids). Suitable examples are tin, titanium, zirconium, which are used in the form of finely divided metals or appropriately in the form of salts thereof (e.g. halides), oxides or soluble or insoluble organic compounds. In contrast to protic acids, the metal catalysts are high-temperature catalysts which often attain their full activity only at temperatures above 180° C. However, it should be noted in this context that the furandicarboxylic acid tends to eliminate $CO_2$ (decarboxylation) at temperatures above 190° C. to form the monocarboxylic acid, which can no longer be converted to the target product.

However, the metal catalysts are used with preference because, compared to protic catalysis, they form a lower level of by-products, for example olefins from the alcohol used. Illustrative representatives of metal catalysts are tin powder, tin(II) oxide, tin(II) oxalate, titanic esters such as tetrapentyl orthotitanate, tetraisopropyl orthotitanate or tetrabutyl orthotitanate, and zirconium esters such as tetrapentyl zirconate or tetrabutyl zirconate.

The catalyst concentration depends on the type of catalyst. In the case of the titanium compounds used with preference, the concentration is 0.005 to 2.0% by mass based on the reaction mixture, especially 0.01 to 0.5% by mass, very preferably 0.01 to 0.1% by mass.

The reaction temperatures in the case of use of titanium catalysts are especially between 160° C. and 270° C., preferably 160° C. to 200° C. The optimal temperatures depend on the feedstocks, reaction progress and catalyst concentration. They can be determined easily by tests for each individual case. Higher temperatures increase the reaction rates and promote side reactions, for example elimination of water from alcohols or formation of coloured by-products. It is favourable for removal of the water of reaction that the alcohol can be distilled out of the reaction mixture. The desired temperature or the desired temperature range can be established by the pressure in the reaction vessel. In the case of low-boiling alcohols the reaction is therefore performed at elevated pressure, and in the case of higher-boiling alcohols under reduced pressure. For example, the reaction of furandicarboxylic acid with a mixture of isomeric pentanols is conducted within a temperature range of 160° C. to 190° C. within the pressure range from 0.1 MPa to 0.001 MPa.

The amount of liquid to be recycled into the reaction may consist partly or entirely of alcohol which can be obtained by workup of the distillate. It is also possible to conduct the workup at a later time and to replace the amount of liquid removed completely or partially with fresh alcohol. i.e. alcohol available in a reservoir vessel.

The crude ester mixtures which comprise, in addition to the pentyl ester(s), alcohol, catalyst or conversion products thereof and possibly by-products are worked up by processes known per se. The workup comprises the following steps: removal of the excess alcohol and any low boilers, neutralization of the acids present, optionally a steam distillation, conversion of the catalyst to a readily filterable residue, removal of the solids and optionally drying. According to the workup process employed, the sequence of these steps may be different.

Optionally, the reaction product can be removed by distillation from the reaction mixture, optionally after neutralization of the mixture.

Alternatively, the inventive pentyl esters can be obtained by transesterifying a furan-2,5-dicarboxylic diester with one or more aliphatic alcohols having 5 carbon atoms. The reactants used are preferably furan-2,5-dicarboxylic diesters whose alkyl radicals bonded to the oxygen atom of the ester group have 1-4 carbon atoms. These radicals may be aliphatic, straight-chain or branched, and alicyclic or aromatic.

One or more methylene groups of these alkyl radicals may be substituted by oxygen. It is appropriate that the parent alcohols of the reactant ester have a lower boiling point than the pentanol(s) used. A preferred feedstock is dimethyl furan-2,5-dicarboxylate.

The use of a furan-2,5-dicarboxylic diester for preparation of the inventive pentyl ester is particularly advantageous because the furan-2,5-dicarboxylic diesters generally have a higher thermal stability than furan-2,5-dicarboxylic acid, and more particularly can also be purified without decomposition by thermal separating processes (for example distillation).

The transesterification can be performed catalytically, for example with Brønsted or Lewis acids or bases. No matter which catalyst is used, the result is always a temperature-dependent equilibrium between the feedstocks (dialkyl ester and pentanol or pentanol mixture) and the products (dipentyl ester or dipentyl ester mixture and alcohol released). In order to shift the equilibrium in favour of the dipentyl ester or of the dipentyl ester mixture, the alcohol formed from the reactant ester is distilled out of the reaction mixture.

It is also appropriate here to use the pentanol mixture in excess.

The transesterification catalysts used may be acids, for example sulphuric acid methanesulphonic acid or p-toluenesulphonic acid, or metals or compounds thereof. Suitable examples are tin, titanium, zirconium, which are used in the form of finely divided metals or appropriately in the form of salts thereof (e.g. halides), oxides or soluble or insoluble organic compounds. Unlike protic acids, the metal catalysts are high-temperature catalysts which attain their full activity only at temperatures above 180° C. However, they are used with preference because they form a lower level of by-products compared to protic catalysis, for example olefins from the alcohol used. Illustrative representatives of metal catalysts are tin powder, tin(II) oxide, tin(II) oxalate, titanic esters such as tetraisopropyl orthotitanate, tetrabutyl orthotitanate or tetrapentyl orthotitanate, and zirconium esters such as tetrabutyl zirconate or tetrapentyl zirconate.

In addition, it is possible to use basic catalysts, for example oxides, hydroxides, hydrogencarbonates, carbonates or alkoxides of alkali metals or alkaline earth metals. From this group, preference is given to using alkoxides, for example sodium methoxide. Alkoxides can also be prepared in situ from an alkali metal and a pentanol or an isomeric pentanol mixture.

The catalyst concentration depends on the type of catalyst. It is typically between 0.005 to 2.0% by mass based on the reaction mixture.

The reaction temperatures for the transesterification are typically between 50° C. and 220° C. They must be at least sufficiently high that the alcohol formed from the reactant ester can be distilled out of the reaction mixture at the given pressure, usually standard pressure.

The transesterification mixtures can be worked up in the same way as described for the esterification mixtures.

In addition to direct esterification and transesterification, the inventive dipentyl furandicarboxylates can also be prepared by means of what is called oxidative esterification. This has the particular advantage that the intermediate of the furandicarboxylic acid or furandicarboxylic ester need not be separated, but rather can be worked up directly with the (semistable) intermediate, for example 5-hydroxymethylfurfural or another furan derivative. An additional factor is that generally low temperatures (i.e. lower tendency to form by-products) and relatively short reaction times are possible.

In order to enable the oxidation reaction, an oxygen-containing component must be present in the reaction mixture. Particularly advantageously suitable for this purpose are oxygen, air and/or peroxides, especially hydrogen peroxide.

The oxidative esterification is more preferably performed in the presence of a catalyst which significantly lowers the reaction time. The catalyst may either be a homogeneous or heterogeneous catalyst. The catalyst—the active catalyst surface in the case of heterogeneous catalysts—more preferably has Lewis acidity. The catalyst is preferably a noble metal catalyst, in the case of a heterogeneous catalyst a noble metal catalyst with nanoscale surface, especially a gold catalyst with nanoscale surface. In the case of heterogeneous catalysts, the use of an inorganic catalyst support is particularly advantageous, particular preference being given to macroporous or microporous supports, especially those which have pore surfaces with nanoscale structure.

In addition to the pentyl ester itself, the use thereof as a plasticizer for polymers is also claimed. The polymer is preferably PVC.

The inventive pentylester can be used particularly advantageously in adhesives, sealing compounds, lacquers, paints, plastisols, synthetic leather, floor coverings, underbody protection, fabric coatings, wallpaper or inks.

In addition, polymer compositions comprising an above-described plasticizer are claimed.

The inventive plasticizers can be used in compositions comprising polymers. These polymers are especially selected from the group consisting of: polyvinyl chloride (PVC), polyvinylidene chloride (PVDC), polyacrylates, especially polymethyl methacrylate (PMMA), polyalkyl methacrylate (PAMA), fluoropolymers, especially polyvinylidene fluoride (PVDF), polytetrafluoroethylene (PTFE), polyvinyl acetate (PVAc), polyvinyl alcohol (PVA), polyvinyl acetals, especially polyvinyl butyral (PVB), polystyrene polymers, especially polystyrene (PS), expandable polystyrene (EPS), acrylonitrile-styrene-acrylate copolymers (ASA), styrene acrylonitrile copolymers (SAN), acrylonitrile-butadiene-styrene copolymers (ABS), styrene-maleic anhydride copolymers (SMA), styrene-methacrylic acid copolymers, polyolefins and/or polyolefin copolymers, especially polyethylene (PE) or polypropylene (PP), thermoplastic polyolefins (TPO), polyethylene-vinyl acetate copolymers (EVA), polycarbonates, polyethylene terephthalate (PET), polybutylene terephthalate (PBT), polyoxymethylene (POM), polyamide (PA), polyethylene glycol (PEG), polyurethane (PU), thermoplastic polyurethane (TPU), polysulphides (PSu), biopolymers, especially polylactic acid (PLA), polyhydroxybutyral (PHB), polyhydroxyvaleric acid (PHV), polyesters, starch, cellulose and cellulose derivatives, especially nitrocellulose (NC), ethylcellulose (EC), cellulose acetate (CA), cellulose acetate/butyrate (CAB), rubber or silicones, and mixtures or copolymers of the polymers mentioned or monomeric units thereof. The inventive polymer compositions preferably comprise PVC or homo- or copolymers based on ethylene, propylene, butadiene, vinyl acetate, glycidyl acrylate, glycidyl methacrylate, methacrylates, ethyl acrylates, butyl acrylates or methacrylates with alkyl radicals, bonded to the oxygen atom of the ester group, of branched or unbranched alcohols having one to ten carbon atom(s), styrene, acrylonitrile or cyclic olefins.

More preferably, the inventive polymer compositions comprise, as the PVC type, suspension, bulk, microsuspension or emulsion PVC.

Based on 100 parts by mass of polymer, the inventive polymer compositions comprise preferably from 5 to 200, more preferably from 10 to 150, parts by mass of plasticizer.

The inventive polymer compositions may comprise, in addition to the constituents mentioned, further constituents which are especially selected from the group consisting of fillers, pigments, thermal stabilizers, costabilizers, antioxidants, viscosity regulators and lubricants.

Thermal stabilizers neutralize, for example, hydrochloric acid eliminated during and/or after the processing of PVC and prevent thermal degradation of the polymer. Useful thermal stabilizers include all customary stabilizers in solid and liquid form, for example based on Ca/Zn, Ba/Zn, Pb, Sn or organic compounds (OBS), and also acid-binding sheet silicates such as hydrotalcite. The inventive mixtures may have a content of 0.5 to 10, preferably 1 to 5 and more preferably 1.5 to 4 parts by mass of thermal stabilizer per 100 parts by mass of polymer.

The so-called costabilizers (i.e. substances which prolong, improve and/or supplement the effect of the thermal stabilizers) used may, for example, be vegetable oil derivatives, for example epoxidized soybean oil or epoxidized linseed oil.

The pigments used in the context of the present invention may be either inorganic or organic pigments. The content of pigments is between 0.01 to 10% by mass, preferably 0.05 to 5% by mass and more preferably 0.1 to 3% by mass per 100 parts by mass of polymer Examples of inorganic pigments are $TiO_2$, CdS, $CoO/Al_2O_3$, $Cr_2O_3$. Known organic pigments are, for example, azo dyes, phthalocyanine pigments, dioxazine pigments and aniline pigments.

The inventive polymer compositions may comprise all fillers corresponding to the prior art Examples of such fillers are mineral and/or synthetic and/or natural, organic and/or inorganic materials, for example calcium oxide, magnesium oxide, calcium carbonate, barium sulphate silicon dioxide, sheet silicate, industrial carbon black, bitumen, wood (e.g. pulverized, as pellets micropellets, fibres, etc.), paper, natural and/or synthetic fibres. More preferably, at least one of the fillers used is a calcium carbonate or a calcium magnesium carbonate.

The viscosity-lowering reagents used may be aliphatic or aromatic hydrocarbons, but also alcohols and/or carboxylic acid derivatives, for example 2,2,4-trimethyl-1,3-pentanediol diisobutyrate. Viscosity-lowering reagents are added to the inventive compositions especially in proportions of 0.5 to 50, preferably 1 to 30 and more preferably 2 to 10 parts by mass per 100 parts by mass of polymer.

The invention further provides mouldings or films produced from or comprising an inventive polymer composition. These mouldings or films are preferably a floor covering, a wall covering, a hose, a profile, a roofing sheet, a sealing sheet, a cable or wire sheath, a tarpaulin, an advertising banner, synthetic leather, packaging film, a medical article, a toy, a seal or a furnishing article.

The inventive pentyl esters, when used as plasticizers, have numerous advantages over known prior art plasticizers. For instance, these compounds are surprisingly, in contrast to the homologous di-n-butyl furandicarboxylates and di-n-hexyl furandicarboxylates, both of which are in the form of crystalline solids with melting points well above room temperature, liquids with good processability (including good meterability).

The production of liquid compositions, especially polymer compositions such as polymer pastes and plastisols, on the industrial scale can best be implemented with liquid plasticizers since the use of solvents here is necessary only in greatly reduced form, if at all. Solvents generally also lead to "dilution" of the plasticizing effect and therefore have to be removed again during the production. Since this can be accomplished quantitatively in the rarest cases, volatile (organic) components called "VOCs" are present in the semifinished or finished products, and are again prohibitive for the use of such products especially in the interior sector and in motor vehicles. An additional factor is the risk of crystallization of solid plasticizers in the semifinished or finished product, which leads to a severe deterioration in the material properties extending as far as material failure. The existing alternative solution to the use of solvents, that of using sod plasticizers in the molten state (i.e. at elevated temperature), cannot be implemented industrially in many cases. There is also the risk of thermal damage to other formulation constituents.

The crystallinity of the inventive esters and the position and type of melting point signals (peaks) and glass transition signals (stages) in the DSC thermogram depend on the degree of branching of the ester chains and the composition of the esters, and are adjustable via the alcohols used to prepare the esters. In the analysis of the inventive pentyl esters (purity by GC analysis at least 98 area %) in a differential calorimeter (DSC) after cooling to $-150°$ C., no melting point occurs at temperatures above 25° C. in the first heating, preferably no melting point at temperatures above 22° C., more preferably no melting point at temperatures above 18° C. and especially preferably no melting point at temperatures above 16° C.

In a particular embodiment, in the analysis by means of DSC described, a glass transition temperature at <0° C. is detected, preferably at <$-10°$ C., more preferably at <$-20°$ C. and especially preferably at <$-30°$ C.

The shear viscosity (intrinsic viscosity) of the inventive esters likewise depends on the degree of branching of the ester chains and the composition of the esters, and is adjustable via the alcohols used to prepare the esters. The shear viscosity, determined at 20° C., of the liquid inventive pentyl esters (purity according to GC analysis at least 98 area %) depends on the degree of branching of the ester chains and the composition of the esters. It is especially not more than 60 mPa*s, preferably not more than 55 mPa's, more preferably not more than 50 mPa's and especially preferably below 46 mPa's.

The density of the inventive esters likewise depends on the degree of branching of the ester chains and the composition of the esters, and is adjustable via the alcohols used to prepare the esters. The density, determined at 20° C., of the inventive esters (purity by GC analysis min. 99 area %) is especially not more than 1.06 $g/cm^3$, preferably not more than 1.05 $g/cm^3$, more preferably not more than 1.03 $g/cm^3$ and especially preferably not more than 1.01 $g/cm^3$.

A further advantage is that the inventive pentyl esters have an outstanding gelation capacity for polymers, especially for PVC, and surprisingly also have a much lower dissolution temperature for PVC than, for example, di-n-butyl furandicarboxylate. PVC pastes based on the inventive furandicarboxylic esters additionally also have a much lower gelation temperature than, for example, the dibutyl terephthalate pastes known from industrial use, even though the inventive esters have longer ester side chains than dibutyl terephthalate. They can thus be processed more rapidly and at lower temperatures.

PVC plastisols/PVC pastes which comprise the inventive pentyl esters in a proportion of at least 10 ma % based on the plasticizers used overall attain (depending on the type and amount of the additionally used plasticizers and solvents), in the gelation test conducted by means of oscillating rheometry with dynamic temperature control (constant heating rate), especially a paste viscosity of >1000 Pa*s at temperatures of not more than 100° C., preferably of not more than 95° C., more preferably of not more than 90° C., especially preferably of not more than 85° C. and very especially preferably of not more than 82° C.

The temperature at which the maximum viscosity is attained in the above-described gelation test is especially not more than 130° C., preferably not more than 120° C., more preferably not more than 118° C., especially preferably not more than 115° C. and very especially preferably not more than 112° C.

It should also be emphasized that PVC pastes based on an inventive pentyl ester have a lower dependency of the paste viscosity on the shear rate than comparable pastes. Thus, these polymer compositions are usable within a wide shear rate range and with a wide variety of different processing methods.

It has additionally also been found that, surprisingly, unfilled transparent PVC films comprising an inventive pentyl ester as a plasticizer have very low opacity and hence high transparency. In some cases, this is much lower than in films which are produced on the basis of standard plasticizers or in which dibutyl terephthalate is used as a plasticizer.

More particularly, in the case of production of transparent films (film thickness 0.9-1.1 mm) from PVC plastisols/PVC pastes comprising an inventive pentyl ester in a proportion of at least 10 ma % based on the plasticizers used overall, opacity values of not more than 15 are achieved, preferably not more than 14, more preferably not more than 13, especially preferably not more than 12 and very especially preferably not more than 11. The yellowness index (Index YD 1925) of the above-described transparent films is especially not more than 18, preferably not more than 16, more preferably not more than 15 and very especially preferably not more than 14.

The examples which follow are intended to illustrate the invention, without restricting the range of application thereof, which is evident from the description and the claims.

EXAMPLES

Example 1

Preparation of furan-2,5-dicarbonyl dichloride (II)

The inventive esters were prepared in a two-stage synthesis proceeding from furan-2,5-dicarboxylic acid via the dichloride. A 250 ml three-neck flask with reflux condenser and dropping funnel was initially charged under argon with 72.1 g (462 mmol) of furan-2,5-dicarboxylic acid. Within a period of 10 min, 165 g (1.39 mol) of thionyl chloride with a few drops of added N,N-dimethylformamide were added. The suspension was heated to reflux temperature and the gas which formed was led off through wash bottles containing aqueous KOH solution. The mixture was then heated under reflux for 4 h until the evolution of gas had ended and the solid had dissolved completely. The product was isolated, after drawing off excess thionyl chloride, by distillative purification (T=110° C., p=0.0012 MPa). This resulted in 79.4 g of dichloride as a colourless crystalline solid (yield 89%) with a melting point of 79.5-80.0° C. Furan-2,5-dicarbonyl dichloride was stored under protective gas (argon) in the dark at room temperature until further use.

Preparation of the furan-2,5-dicarboxylic esters from furan-2,5-dicarbonyl dichloride (II)

Under argon, a three-neck flask with reflux condenser and dropping funnel was initially charged with the dichloride which was melted by heating. 2.4 equivalents of n-pentanol were slowly added dropwise to the liquid, which resulted in an exothermic reaction with evolution of gas. The gas formed was passed through wash bottles containing aqueous KOH solution. After complete addition, the mixture was stirred at a temperature of 80-100° C. for 16 h.

The excess alcohol was removed under reduced pressure in the presence of boiling granules, and the crude product was purified by distillation. This gave dipentyl furan-2,5-dicarboxylate, which was used for the further experiments.

Characterization of the dipentyl furan-2,5-dicarboxylate 1.1 Determination of Ester Purity by Means of Gas Chromatography Analysis (GC)

The determination of the purity of the esters prepared by means of GC is effected with a "6890N" GC machine from Agilent Technologies using a DB-5 column (length: 20 m, internal diameter: 0.25 mm, film thickness 0.25 µm) from J&W Scientific and a flame ionization detector under the following boundary conditions:

| | |
|---|---|
| Oven start temperature: 150° C. | Oven end temperature: 350° C. |
| (1) Heating rate 150-300° C.: 10 K/min | (2) Isothermal: 10 min. at 300° C. |
| (3) Heating rate 300-350° C.: 25 K/min. | |
| Total run time: 27 min. | |
| Injection block entrance temperature: 300° C. | Split ratio: 200:1 |
| Split flow rate: 512.2 ml/min | Total flow rate: 517.7 ml/min. |
| Carrier gas: helium | Injection volume: 3 microlitres |
| Detector temperature: 350° C. | Combustion gas: hydrogen |
| Hydrogen flow rate: 40 ml/min. | Air flow rate: 440 ml/min. |
| Makeup gas: helium | Makeup gas flow rate: 45 ml/min. |

The gas chromatograms obtained are evaluated manually against comparative substances present; the purity is reported in area percent. Due to the high final contents of target substance of >98%, the expected error resulting from lack of calibration for the particular test substance is low.

The measurement gave a purity of the ester prepared in Example 1 of 98.9 area %.

1.2 Determination of the Density of the Ester Prepared

The density of the esters prepared was determined by means of an oscillating U-tube to DIN 51757—method 4.

The measurement gave a density of 1.0468 g/cm$^3$.

1.3 Determination of the APHA Colour Number of the Ester Prepared

The colour number of the esters prepared was determined to DIN EN ISO 6271-2.

The measurement gave an APHA colour number of 41.

1.4 Determination of the Acid Number of the Ester Prepared

The acid number of the esters prepared was determined to DIN EN ISO 2114.

The determination gave an acid number of 0.16 mg KOH/g.

1.5 Determination of the Water Content of the Ester Prepared

The water content of the esters prepared was determined to DIN 51777 Part 1 (direct method).

The determination gave a water content of 0.042%.

1.6 Determination of the Intrinsic Viscosity of the Ester Prepared

The intrinsic viscosity (shear viscosity) of the ester prepared was determined using a Physica MCR 101 (from Anton-Paar) with a Z3 measurement system (DIN 25 mm) in rotation mode, by means of the following method:

Ester and measurement system were first equilibrated to a temperature 20° C., then the following actions were executed:
1. Preliminary shear at 100 s$^{-1}$ for a period of 60 s, in the course of which no measurements were recorded (to level out any thixotropic effects which occur and for better temperature distribution).

2. An upward frequency ramp commencing at 500 s$^{-1}$ and ending at 10 s$^{-1}$, divided into a logarithmic series of 20 steps each with measurement point duration 5 s (verification of newtonian behaviour).

The ester exhibited newtonian flow behaviour.

The measurement gave a shear viscosity (at 42 s$^{-1}$) of 44 mPa*s.

1.7 Determination of Glass Transition Temperature and Melting Point of the Ester Prepared by Means of DSC The glass transition temperature and the melting point were determined by means of differential calorimetry (DSC) to DIN 51007 (temperature range from −150° C. to +200° C.) from the first heating curve at a heating rate of 10 K/min. The turning point of the heat flow curve is evaluated as the glass transition temperature.

The measurement gave a glass transition temperature of −34° C. and a melting point of +12° C. the sample had been stored in liquid form at room temperature for 7 days beforehand.

Example 2

Dissolution Temperature of the Plasticizers

The dissolution temperature states the temperature from which a PVC powder dispersed in a continuously heated plasticizer excess (96 g of plasticizer to 4 g of polymer) is dissolved, and permits conclusions about the gelling characteristics. Di-n-butyl furan-2,5-dicarboxylate (DNBFDC) and di-n-hexyl furan-2,5-dicarboxylate (DNHFDC) were prepared using n-butanol and n-hexanol respectively, analogously to Example 1. The di-n-butyl furan-2,5-dicarboxylate and di-n-hexyl furan-2,5-dicarboxylate solids were first melted at 50° C., and the inventive di-n-pentyl furan-2,5-dicarboxylate (DNPFDC) was heated to 50° C., before the PVC powder was dispersed in liquid and the temperature was increased.

Test Procedure:

96 g of the appropriate plasticizer and 4 g of the PVC Lacovyl PB 1704 H (from Arkema) are weighed into a 150 ml beaker. A magnetic stirrer bar and an internal thermometer secured to a clamp stand (range: 0° C.-250° C., display accuracy: 0.5° C.) are added to the mixture. A wire or adhesive tape is used to secure a paper strip which the message "Lösetemperatur" in the font "Times New Roman", font size 12, to the reverse side of the beaker such that the message can be seen through the beaker. Thereafter, the hotplate of a heatable laboratory stirrer unit (MR -Hei-Standard) is set to 200° C. and the speed to 600 rpm. On attainment of an internal temperature of the liquid of 140° C., the target temperature was once again raised to 250° C. The dissolution temperature has been attained when the message is just clearly readable through the liquid.

For DNBFDC, DNPFDC and DNHFDC, the following values shown in Table 1 were determined (double determination):

TABLE 1

Results of the tests of dissolution temperature

| Plasticizer | Dissolution temperature [° C.] |
|---|---|
| DNBFDC | 117 |
| DNPFDC* | 96 |
| DNHFDC | 104 |

*inventive

Entirely surprisingly, the dissolution temperature of the inventive DNPFDC is well below that of the homologous DNBFDC. As the tests which follow show, DNPFDC has a much better gelation capacity.

Example 3

Use of the Inventive Dipentyl Furandicarboxylates in a PVC Plastisol for Production of Topcoat Films for Floor Coverings Production of the Plastisols The advantageous properties achievable with the inventive plasticizers are to be illustrated hereinafter using plastisols/pastes as used, for example, for production of a transparent top layer (called "topcoat") in floor coverings of multilayer structure. The starting weights used, in grams, of the components for the different pastes can be found in Table 2 below. Examples 3 and 6 are inventive; the other Examples 1, 2, 4, 5, 7 and 8 are comparative examples.

TABLE 2

Formulations (all figures in parts by mass)

| Paste formulation | 1 | 2 | 3* | 4 | 5 | 6* | 7 | 8 |
|---|---|---|---|---|---|---|---|---|
| Vestolit B 7021-Ultra | 100 | 100 | 100 | 100 | 100 | 100 | 100 | 100 |
| Vestinol ® 9 | 50 | | | | 25 | 25 | 25 | |
| DNBFDC | | 50 | | | 25 | | | |
| DNPFDC | | | 50 | | | 25 | | |
| DNHFDC | | | | 50 | | | 25 | |
| Eastman DBT | | | | | | | | 50 |
| Drapex 39 | 3 | 3 | 3 | 3 | 3 | 3 | 3 | 3 |
| Mark CZ 149 | 2 | 2 | 2 | 2 | 2 | 2 | 2 | 2 |

*= inventive

The substances used are described hereinafter:

Vestolit B 7021-Ultra: microsuspension PVC (homopolymer) with a K value (determined to DIN EN ISO 1628-2) of 70; from Vestolit GmbH.
Vestinol ® 9: diisononyl (ortho)phthalate (DINP), plasticizer; from Evonik Oxeno GmbH.
DNBFDC: di-n-butyl furan-2,5-dicarboxylate (prepared with n-butanol analogously to Example 1)
DNPFDC: inventive dipentyl furandicarboxylate according to Ex. 1
DNHFDC: di-n-hexyl furan-2,5-dicarboxylate (prepared with n-hexanol analogously to Example 1)
Eastman DBT: dibutyl terephthalate, plasticizer with rapid gelation, from Eastman Chemicals
Drapex 39: epoxidized soybean oil; costabilizer with plasticizing action; from Galata Chemicals.
Mark CZ 149: Ca/Zn stabilizer, from Galata Chemicals The liquid constituents were weighed into a PE beaker before the solid constituents. The mixture was stirred with an ointment spatula such that no unwetted powder was present any longer. The mixing beaker was then clamped into the clamping device of a dissolver stirrer. A mixer disc was used to homogenize the sample. This was done by increasing the speed from 330 rpm to 2000 rpm and stirring until the temperature on the digital display of the temperature sensor reached 30.0° C. This reliably ensured that the homogenization of the paste had been achieved with a defined energy input. Thereafter, the paste was equilibrated immediately at 25.0° C.

Formulations 2 and 4 were producible only by heating the furandicarboxylates present in solid form. After the preparation, however, the pastes solidified to such a degree that no further processing was possible.

Paste 6 exhibits the mode of action of an inventive di-n-pentyl furandicarboxylate in blends with a further plasticizer.

Example 4

Use of the Inventive Dipentyl Furandicarboxylates in a PVC Plastisol for Production of Topcoat Films for Floor Coverings: Measurement of Paste Viscosity The measurement of the viscosities of the pastes produced in Example 3 was conducted with a Physica MCR 101 rheometer (from Anton Paar), as follows.

The paste which had been stored after production at 25° C. for 24 h was homogenized once again with a spatula and analyzed in the Z3 measurement system (diameter 25 mm) according to the operating instructions. The measurement was conducted isothermally at 25° C. The following actions were executed.

Preliminary shear of 100 s$^{-1}$ for a period of 60 s, in which no measurements were recorded (levelling out of thixotropic effects).

An isothermal downward ramp, commencing at a shear rate of 200 s$^{-1}$ down to 0.1 s$^{-1}$, divided into a logarithmic series with 30 steps each of measurement point duration 5 s. The results of the measurement are shown in Table 3.

TABLE 3

Results of the viscosity measurements (shear rate profile)

| Plastisol formulation according to Ex. 3 | 1 | 2 | 3* | 4 | 5 | 6* | 7 | 8 |
|---|---|---|---|---|---|---|---|---|
| Shear viscosity at shear rate = 100/s [Pa * s] | 9.8 | n.da. | 15.8 | n.da. | 8.1 | 6.9 | 6.5 | 3.9 |
| Shear viscosity at shear rate = 10/s [Pa * s] | 4.7 | n.da. | 10.3 | n.da. | 4.6 | 3.7 | 3.6 | 2 2 |
| Shear viscosity at shear rate = 1/s [Pa * s] | 4.6 | n.da. | 10 | n.da. | 4.4 | 3.5 | 3.5 | 2.4 |
| Shear viscosity at shear rate = 0.1/s [Pa * s] | 3.4 | n.da. | 13.4 | n.da. | 5.5 | 4.4 | 4.4 | 3.4 |
| Range of variation [%] (Max. visco − min. visco/min. visco) * 100 | 188 | n.da. | 58 | n.da. | 84 | 97 | 85 | 77 | n.da.: not determinable; paste severely solidified; measurement impossible.
*= inventive Compared to the pastes comprising only one plasticizer substance (pastes 1, 2, 3, 4, 8), the inventive paste has by far the smallest range of variation of the paste viscosity. This result is surprising especially in the comparison between the inventive dipentyl furandicarboxylate and the structurally similar dibutyl terephthalate. A blend of the standard plasticizer Vestinol 9 with the inventive dipentyl furandicarboxylate (paste 6) leads to a very significant reduction in the range of variation compared to a paste comprising Vestinol 9 alone as a plasticizer (paste 1). The general increase in the viscosity level of the inventive pastes can be matched easily by the person skilled in the art to the circumstances present in the particular processing method, for example by adding viscosity additives or solvents.

Example 5

Use of the Inventive Dipentyl Furandicarboxylates in a PVC Plastisol for Production of Topcoat Films for Floor Coverings: Determination of Gelation Characteristics (Gelation Rate)

The study of the gelation characteristics of the plastisols was conducted in the Physica MCR 101 in oscillation mode with a plate-plate measurement system (PP25), which was operated under shear stress control. An additional temperature control hood was attached to the system in order to achieve homogeneous heat distribution.

Measurement Parameters:
Mode: Temperature Gradient (Temperature Ramp)
Start temperature: 25° C.
End temperature: 180° C.
Heating/cooling rate: 5 K/min
Oscillation frequency: 4-0.1 Hz ramp (logarithmic)
Angular frequency omega: 10 1/s
Number of measurement points: 63
Measurement point duration: 0.5 min
Automatic gap readjustment F: 0 N
Constant measurement point duration
Gap width 0.5 mm Measurement Procedure:

A drop of the plastisol formulation to be analyzed, free of air bubbles, was applied to the lower measurement system plate. It was ensured that, after the closure of the measurement system, some plastisol could exude uniformly out of the measurement system (not more than approx 6 mm overall). Subsequently, the temperature control hood was positioned over the sample and the measurement was started.

The "complex viscosity" of the plastisol was determined as a function of temperature. Onset of the gelation process was noticeable by a sudden sharp rise in the complex viscosity. The sooner the onset of this viscosity rise, the better the gelation capacity of the system.

By interpolating for each plastisol, the measurement curves obtained were used to determine the temperatures at which a complex viscosity of 1000 Pa·s or 10 000 Pa*s had been attained. In addition, by means of the tangent method, the maximum plastisol viscosity attained in the present test setup was determined, and, by dropping a perpendicular, the temperature from which the maximum plastisol viscosity occurs. The results are compiled in Table 4.

TABLE 4

Results of the gelation tests

| Plastisol formulation (according to Ex. 3) | 1 | 2 | 3* | 4 | 5 | 6* | 7 | 8 |
|---|---|---|---|---|---|---|---|---|
| Attainment of a plastisol viscosity of 1000 Pa * s at [° C.] | 87 | n.da. | 63 | n.da. | 68 | 72 | 75 | 65 |

TABLE 4-continued

Results of the gelation tests

| Plastisol formulation (according to Ex. 3) | 1 | 2 | 3* | 4 | 5 | 6* | 7 | 8 |
|---|---|---|---|---|---|---|---|---|
| Attainment of a plastisol viscosity of 10 000 Pa * s at [° C.] | 97 | n.da. | 66 | n.da. | 73 | 76 | 80 | 68 |
| Maximum plastisol viscosity [Pa * s] | 26900 | n.da. | 120000 | n.da. | 71900 | 63000 | 46700 | 91400 |
| Temperature on attainment of the maximum plastisol viscosity [° C.] | 137 | n.da. | 82 | n.da. | 85 | 87 | 90 | 83 | n.da.: not determinable; paste severely solidified; measurement impossible.
*= inventive Compared to the pastes comprising only one plasticizer substance (pastes 1, 2, 3, 4, 8), the inventive paste has the fastest gelation (i.e., here too, gelation at the lowest temperatures) Compared to the standard plasticizer Vestinol® 9, the inventive di-n-pentyl furan-2.5-dicarboxylate (DNPFDC) is found to be a "fast gelator", i.e. a compound which has gelation capacity at much lower temperatures than standard plasticizers. The DNPFDC paste actually gelates somewhat more rapidly than the paste comprising Eastman DBT, a substance with similar structure and shorter ester chains. This is all the more surprising in that the gelation capacity in the case of aromatic dicarboxylic esters (e.g. orthophthalates, terephthalates, etc.) generally increases with falling chain length. By blending the inventive dipentyl furandicarboxylate with the standard plasticizer Vestinol 9, a significant acceleration (compared to pure Vestinol® 9) of the gelation process (especially with regard to the temperature at which the maximum viscosity is attained) is enabled.

It is also clearly evident that the gelation process of the inventive paste 3 leads to a very much higher final viscosity than is the case for all other pastes. The use of the inventive dipentyl furandicarboxylate thus also leads, in the fully gelated state, to outstanding material properties (especially strengths) in the semifinished or finished product/moulding produced.

Example 6

Use of the Inventive Dipentyl Furandicarboxylates in a PVC Plastisol for Production of Topcoat Films for Floor Coverings: Determination of the Shore A Hardness of Castings (Plasticizer Efficiency)

The Shore hardness is a measure of the softness of a test specimen. The further a standardized needle can penetrate into the test specimen with a particular measurement duration, the lower the measurement is. The plasticizer with the highest efficiency gives the lowest Shore hardness value for the same amount of plasticizer. Since formulations/recipes in practice are frequently adjusted or optimized toward a particular Shore hardness, it is accordingly possible in the case of very efficient plasticizers to dispense with a particular proportion in the formulation, which means, for example, a reduction in costs for the processor.

To determine Shore hardnesses, the plastisols produced according to Example 3 were poured into round brass casting moulds with a diameter of 42 mm (starting weight: 20.0 g). Then the plastisols were gelated in the moulds in a forced-air drying cabinet at 200° C. for 30 min, removed after cooling and, before the measurement, stored in a drying cabinet (25° C.) for at least 24 hours. The thickness of the discs was approx. 12 mm. The results of the hardness determination are compiled in Table 5.

TABLE 5

| Plastisol formulation (according to Ex. 3) | 1 | 2 | 3* | 4 | 5 | 6* | 7 | 8 |
|---|---|---|---|---|---|---|---|---|
| Shore A | 82 | n.da. | 72 | n.da. | 75 | 76 | 77 | 73 | n.da. = not determinable; paste severely solidified; no casting producible.
*= inventive Compared to the pastes comprising only one plasticizer substance (pastes 1, 2, 3, 4, 8), the casting produced from the inventive paste 3 has the lowest Shore A hardness and is thus "the softest". This also means that the efficiency of the inventive dipentyl furandicarboxylate with regard to the plasticization of PVC in the paste is surprisingly the highest, and is actually higher than that of dibutyl terephthalate (paste 8). This is astonishing in that—similarly to the gelation capacity—the plasticizing action in the case of aromatic dicarboxylic esters (e.g. orthophthalates, terephthalates, etc.) generally increases with falling chain length.

Example 7

Use of the Inventive Dipentyl Furandicarboxylates in a PVC Plastisol for Production of Topcoat Films for Floor Coverings: Determination of Transparency and Yellowness Index of the Transparent Topcoat Films The films were produced after a maturing time of the plastisols of 24 hours (at 25° C.). For the film production, a roll nip of 1.40 mm was established on the doctor roll of a Mathis Labcoater (manufacturer: W. Mathis AG). This nip was monitored by a feeler gauge and readjusted as necessary. The pastes produced were doctored onto a high-gloss paper (Ultracast Patent: from Sappi Ltd.) clamped flat in a frame by means of the doctor roll of the Mathis Labcoater. The plastisol applied by doctoring was then gelated fully at 200° C. in the Mathis oven for 2 min. After cooling, the film thickness was determined with an accuracy of 0.01 mm with the aid of a rapid thickness gauge (KXL047; from Mitutoyo). The film thickness of this film at the roll nip specified was in all cases between 0.95 and 1.05 mm. The measurement of the thickness was conducted at three different points on the film.

Transparency is an important criterion for assessing the quality of PVC topcoats in the flooring sector, since an optimal overall appearance can be achieved only with high transparency (=low opacity). The transparency of a PVC topcoat film is also considered to be a measure of the compatibility of the formulation constituents used for film production, more particularly to be a measure for assessing the compatibility of PVC matrix and plasticizer. High transparency (=low opacity) generally means good compatibility. The opacity was determined with a "Spectro Guide" instrument from Byk Gardner. As a background for the opacity measurements, a white tile and a black tile were used. The measurements were conducted at 3 different points on the samples and evaluated automatically (average value).

The yellowness index is a further important quality criterion. Yellowing in the topcoat can lead to considerable visual impairment of a floor finish, and therefore only very low yellowness indices can generally be tolerated in a PVC topcoat. The yellowing can be caused firstly by formulation constituents (and also by the by-products and degradation products thereof), and secondly by degradation (for example thermooxidative) during the production process and/or during the use of the topcoat or of the floor covering.

The yellowness index (index YD 1925) is a measure of the yellowing of a test specimen. The colour was analyzed with a "Spectro Guide" instrument from Byk-Gardner. As a background for the colour measurements, a white reference tile was used. The following parameters were set
Illuminant: C/2°
Number of measurements: 3
Display: CIE L*a*b*
Index measured: YD1925

The measurements themselves were conducted at 3 different points on the samples. The values from the 3 measurements were averaged. Table 6 shows the results.

TABLE 6

Opacity and yellowness indices of transparent topcoat films

| Plastisol formulation (according to Ex. 3) | 1 | 2 | 3* | 4 | 5 | 6* | 7 | 8 |
|---|---|---|---|---|---|---|---|---|
| Opacity [–] | 10.2 | — | 10.6 | — | 10.4 | 10.3 | 10.1 | 12.1 |
| Yellowness index [–] | 9.4 | — | 13.0 | — | 10.7 | 10.7 | 8.8 | 8.9 |

*= inventive

Examples 2 and 4 could not be determined because the plastisols were too hard (i.e. unsuitable) for production of topcoat films. Compared to the individual substances (1, 3 and 8), the topcoat film produced from the inventive DNPFDC paste (3) exhibits very high transparency (low opacity), especially compared with that produced on the basis of Eastman DBT. This is astonishing in that—similarly to the gelation capacity—the compatibility of the plasticizer with the PVC matrix (crucial for transparency) generally increases with falling chain length in the case of aromatic dicarboxylic esters (e.g. orthophthalates, terephthalates, etc.), since the nonpolar proportion decreases at the same time. What is particularly remarkable is the small difference from the standard plasticizer DINP (1), which indicates excellent compatibility of the inventive DNPFDC with the PVC matrix. The slightly increased yellowness index in the case of the topcoat film produced from the inventive DNPFDC is attributable to the renewable raw materials (sugars or carbohydrate derivatives) used for production of the inventive product, and can be lowered in a simple manner by the person skilled in the art, by further optimizing the production process or selecting an (additional) optimized stabilizer.

Example 8

Use of the Inventive Dipentyl Furandicarboxylates in a PVC Plastisol for Production of Polymer Foams for Floor Coverings: Production of the Plastisols In the example which follows, mixtures of the inventive dipentyl furandicarboxylates with other plasticizers are presented in formulations as used, for example, for the production of multilayer floor coverings. Pastes with the composition as specified in Table 7 below were produced. The pastes were produced analogously to the procedure described in Example 3.

TABLE 7

Paste formulations (all figures in parts by mass)

| Pastes | 1 | 2 | 3 | 4 | 5 | 6 |
|---|---|---|---|---|---|---|
| Vinnolit MP 6852 | 100 | 100 | 100 | 100 | 100 | 100 |
| Vestinol ® 9 | 59 | | | | | |
| DINFDC | | 54 | 49 | 44 | | |
| DINT | | | | | 44 | |
| Hexamoll ® DINCH | | | | | | 44 |
| DNPFDC* | | 5 | 10 | 15 | 15 | 15 |
| Unifoam AZ Ultra 7043 | 3 | 3 | 3 | 3 | 3 | 3 |
| ZnO masterbatch 1:2 DINP | 2 | 2 | 2 | 2 | 2 | 2 |

*= inventive plasticizer
The substances used are explained in detail hereinafter:
Vinnolit MP 6852: microsuspension PVC (homopolymer) with K value (to DIN EN ISO 1628-2) of 68; from Vinnolit GmbH & Co KG.
Vestinol ® 9: diisononyl (ortho)phthalate (DINP), plasticizer; from Evonik Oxeno GmbH.
Unifoam AZ Ultra 7043: azodicarbonamide; thermally activatable blowing agent; from Hebron S.A.
Zinc oxide: ZnO; decomposition catalyst for thermal blowing agent; lowers the intrinsic decomposition temperature of the blowing agent; also acts simultaneously as a stabilizer; "Zinkoxid aktiv ®"; from Lanxess AG. The zinc oxide was premixed with a sufficient portion/amount of the particular plasticizer used and then added.
DINFDC: diisononyl furandicarboxylate, laboratory product; preparation analogous to Example 1, except using isononyl alcohol (from Evonik Oxeno GmbH)
DINT: diisononyl terephthalate; laboratory product; prepared according to WO 2009/095126 A1 from isononyl alcohol (from Evonik Oxeno GmbH)
Hexamoll ® DINCH: diisononyl cyclohexanecarboxylate; from BASF SE
DNPFDC: di-n-pentyl furan-2,5-dicarboxylate according to Example 1

Example 9

Use of the Inventive Dipentyl Furandicarboxylates in a PVC Plastisol for Production of Polymer Foams for Floor Coverings: Determination of Paste Viscosity The paste viscosity was determined as described in Example 4; the results are shown in Table 8.

TABLE 8

| Plastisol formulation according to Ex. 8 | 1 | 2* | 3* | 4* | 5* | 6* |
|---|---|---|---|---|---|---|
| Shear viscosity at shear rate = 100/s [Pa * s] | 3.1 | 6.4 | 6.6 | 7.1 | 3.3 | 2.6 |
| Shear viscosity at shear rate = 10/s [Pa * s] | 2.5 | 5.3 | 5.6 | 6.1 | 2.6 | 2.3 |
| Shear viscosity at shear rate = 1/s [Pa * s] | 2.9 | 5.8 | 6.2 | 6.9 | 2.9 | 2.9 |
| Shear viscosity at shear rate = 0.1/s [Pa * s] | 4.3 | 8.1 | 8.8 | 10.1 | 4.2 | 4.7 |

*= inventive

The results show that especially mixtures with plasticizers such as the terephthalate DINT and with DINCH lead to low paste viscosities and very good processing properties. These are much better than for the comparative product Vestinol® 9; especially by blending with DINCH, It is possible to establish a very low paste viscosity which is also suitable for very high-speed processing methods (for example in the case of doctor application). In a particularly to advantageous manner, these blends combine good processability, freedom from phthalates and particularly high sustainability (with regard to the raw material basis of the inventive dipentyl furandicarboxylates).

Example 10

Use of the Inventive Dipentyl Furandicarboxylates in a PVC Plastisol for Production of Polymer Foams for Floor Coverings: Determination of Gelation Properties (Gelation Rate)

The gelation properties were determined as described in Example 5, except using the plastisols produced according to Example 8. The results are shown in Table 9.

TABLE 9

| Plastisol formulation (according to Ex. 8) | 1 | 2* | 3* | 4* | 5* | 6* |
|---|---|---|---|---|---|---|
| Attainment of a plastisol viscosity of 1000 Pa * s at [° C.] | 83 | 78 | 76 | 74 | 81 | 78 |
| Attainment of a plastisol viscosity of 10 000 Pa * s at [° C.] | 88 | 82 | 80 | 78 | 97 | 83 |
| Maximum plastisol viscosity [Pa * s] | 26300 | 32500 | 38300 | 46600 | 23100 | 22600 |
| Temperature on attainment of maximum plastisol viscosity [° C.] | 130 | 100 | 90 | 86 | 128 | 125 |

*= inventive

Compared to the standard plasticizer Vestinol® 9, all blends of the inventive furandicarboxylic esters exhibit a distinct improvement in gelation characteristics with gelation at much lower temperatures in some cases. With increasing concentration of inventive ester, the gelation rate increases, the maximum achievable viscosity increases significantly and the gelation temperature decreases significantly. By blending the (very slowly gelating) DINCH (paste 5) with the inventive ester, gelation characteristics very similar to those of the standard plasticizer Vestinol® 9 are established. By adding the inventive furandicarboxylic ester, processability is thus distinctly improved; more particularly, it is possible to process such pastes more rapidly or at lower temperatures.

Example 11

Use of the Inventive Dipentyl Furandicarboxylates in a PVC Plastisol for Production of Polymer Foams for Floor Coverings: Determination of Foaming Characteristics The foaming characteristics were determined to an accuracy of 0.01 mm with the aid of a rapid thickness gauge suitable for soft PVC measurements (KXL047, from Mitutoyo). For the film production, a roll nip of 1 mm was established on the doctor roll of a Mathis Labcoater (model: LTE-TS; manufacturer: W. Mathis AG). This nip was monitored with a feeler gauge and readjusted as necessary. The pastes were doctored onto a release paper (Warran Release Paper; from Sappi Ltd.) clamped flat in a frame by means of the doctor roll of the Mathis Labcoater. In order to be able to calculate the percentage foaming, a partially gelated and unfoamed film was first produced at 200° C./residence time 30 seconds. The film thickness (starting thickness) of this film at the specified roll nip was in all cases between 0.74 and 0.77 mm. The measurement of the thickness was conducted at three different points on the film. Subsequently, the foamed films (foams) were likewise produced with an oven residence time (60 s, 90 s, 120 s and 150 s) using the, or more specifically in the, Mathis Labcoater. After cooling the foams, the thicknesses were likewise measured at three different points. The average of the thicknesses and the starting thickness were required for the calculation of expansion. (Example (foam thickness−starting thickness)/starting thickness*100%= expansion). The results are shown in Table 10.

TABLE 10

Expansion characteristics of the foam films

| Plastisol formulation (according to Ex. 8) | 1 | 2* | 3* | 4* | 5* | 6* |
|---|---|---|---|---|---|---|
| Expansion after 60 s @ 200° C. [%] | 22 | 8 | 8 | 8 | 8 | 1 |
| Expansion after 90 s @ 200° C. [%] | 305 | 299 | 278 | 292 | 285 | 265 |
| Expansion after 120 s @ 200° C. [%] | 386 | 414 | 407 | 414 | 407 | 393 |
| Expansion after 150 s @ 200° C. [%] | 407 | 441 | 414 | 427 | 414 | 407 |

*= inventive

The foaming of the pastes which comprise inventive furandicarboxylic ester proceeds much more quickly than with the standard plasticizer Vestinol® 9 and leads to higher foam heights. This also applies to the blend with DINCH and the terephthalate DINT.

Example 12

Use of the Inventive Dipentyl Furandicarboxylates in a Mixture with Additional Plasticizers for Production of Tarpaulins: Production of the Plastisols The advantages of the inventive pastes are to be illustrated hereinafter using PVC pastes which comprise filler and pigment and are suitable for production of tarpaulins (for example as a basecoat for flow impregnation). In the appropriate application, the present formulation can be matched to the particular requirements in a simple manner, for example by adding adhesion promoters and/or flame retardants. The pastes were produced analogously to Example 3, but with an altered formulation. The starting weights of the components used for the different pastes can be found in Table 11 below. All figures in parts by mass.

TABLE 11

Plastisol formulations

| Formulation: | 1 | 2* | 3* | 4* | 5* | 6* |
|---|---|---|---|---|---|---|
| Vestolit P 1430 K70 | 100 | 100 | 100 | 100 | 100 | 100 |
| Vestinol ® 9 | 50 | | | | | |
| DINFDC | | 45 | 40 | 35 | | |
| DINT | | | | | 35 | |
| Hexamoll ® DINCH | | | | | | 35 |
| DNPFDC | | 5 | 10 | 15 | 15 | 15 |
| Calcilit 6G | 15 | 15 | 15 | 15 | 15 | 15 |
| Kronos 2220 | 3 | 3 | 3 | 3 | 3 | 3 |

TABLE 11-continued

Plastisol formulations

| Formulation: | 1 | 2* | 3* | 4* | 5* | 6* |
|---|---|---|---|---|---|---|
| Drapex 39 | 3 | 3 | 3 | 3 | 3 | 3 |
| Mark BZ 561 | 1.5 | 1.5 | 1.5 | 1.5 | 1.5 | 1.5 |

*= inventive

The materials and substances used which are not already explained in the preceding examples are explained in detail hereinafter:
Vestolit P 1430 K70: microsuspension PVC from Vestolit GmbH
DNPFDC: inventive dipentyl furandicarboxylate according to Ex. 1
Calcilit 6G: filler; calcium carbonate
Kronos 2220: rutile pigment from Kronos
Mark BZ 561: Ba/Zn stabilizer from Galata Chemicals Example 13

Use of the Inventive Dipentyl Furandicarboxylates in a Mixture with Additional Plasticizers for Production of Tarpaulins: Determination of Plastisol Viscosity The paste viscosity was determined as described in Example 4; the results are shown in Table 12.

TABLE 12

Results of viscosity measurements (shear rate profile)

| Plastisol formulation according to Ex. 12 | 1 | 2* | 3* | 4* | 5* | 6* |
|---|---|---|---|---|---|---|
| Shear viscosity at shear rate = 100/s [Pa * s] | 8.9 | 15 | 14.9 | 15.8 | 9.3 | 5.7 |
| Shear viscosity at shear rate = 10/s [Pa * s] | 5.1 | 9 | 9.1 | 10.1 | 5.1 | 4 |
| Shear viscosity at shear rate = 1/s [Pa * s] | 6.3 | 9.7 | 9.9 | 11.4 | 6 | 5.1 |
| Shear viscosity at shear rate = 0.1/s [Pa * s] | 11.7 | 15.1 | 15.7 | 18.5 | 11.2 | 9.8 |

*= inventive

In blends with the terephthalate DINT and with DINCH, much lower plastisol viscosities are attained in some cases than with the standard plasticizer Vestinol® 9; it is thus possible to process these plastisols much more rapidly in spreading processes than, for example, plastisols based purely on Vestinol® 9.

Example 14

Use of the Inventive Dipentyl Furandicarboxylates in a Mixture with Additional Plasticizers for Production of Tarpaulins: Determination of Gelation Characteristics The gelation characteristics were determined as described in Example 5, but using the plastisols produced according to Example 12. The results are shown in Table 13.

TABLE 13

Results of the gelation tests

| Plastisol formulation (according to Ex. 12) | 1 | 2* | 3* | 4* | 5* | 6* |
|---|---|---|---|---|---|---|
| Attainment of a plastisol viscosity of 1000 Pa * s at [° C.] | 83 | 78 | 75 | 73 | 78 | 76 |
| Attainment of a plastisol viscosity of 10 000 Pa * s at [° C.] | 88 | 82 | 79 | 77 | 86 | 83 |
| Maximum plastisol viscosity [Pa * s] | 33900 | 39300 | 44600 | 56600 | 29300 | 26900 |
| Temperature on attainment of maximum plastisol viscosity [° C.] | 136 | 126 | 88 | 85 | 132 | 134 |

*= inventive

In all cases, gelation is much more rapid than in the case of the standard plasticizer Vestinol® 9. With a rising proportion of inventive dipentyl furandicarboxylate, especially in combination with diisononyl furandicarboxylate (samples 2-4), there is a very rapid acceleration of the gelation process, as evident particularly from the temperature at which the maximum viscosity is attained. In combination with the terephthalate DINT and with DINCH, gelation properties which are still better than those of the standard plasticizer Vestinol® 9 are achieved.

Example 15

Use of the Inventive Dipentyl Furandicarboxylates in a Mixture with Additional Plasticizers for Production of Tarpaulins: Determination of Plasticizer Efficiency (Shore A)

The castings were produced and the Shore hardness was measured analogously to the procedure described in Example 6. The results are shown in Table 14.

TABLE 14

Plastisol formulations

| Plastisol formulation (according to Ex. 12) | 1 | 2* | 3* | 4* | 5* | 6* |
|---|---|---|---|---|---|---|
| Shore A | 81 | 78 | 77 | 75 | 78 | 77 |

*= inventive

All mixtures attain Shore A values below the value for the standard plasticizer Vestinol 9. The plasticizing action of all samples comprising the inventive pentyl esters is thus greater than that of the standard plasticizer. The plasticizing action additionally increases distinctly with the concentration of the inventive pentyl esters. In blends with the terephthalate DINT and with DINCH, lower Shore A values are also achieved than with Vestinol® 9. It is accordingly possible for the person skilled in the art to distinctly reduce the total amount of plasticizer by using the inventive pentyl esters.

The invention claimed is:

1. A mixture of isomeric furandicarboxylic acid pentyl esters.
2. The mixture according to claim 1, wherein the esters of furandicarboxylic acid comprise a dipentyl ester.
3. The mixture according to claim 1, wherein the esters of furandicarboxylic acid have at least one of the following properties:

a density at 20° C. of not more than 1.06 g/cm³, an intrinsic viscosity at 25° C. of not more than 60 mPa·s; and no melting signal at temperatures >25° C. when analysed with a differential calorimeter.

4. The mixture according to claim 3, wherein the esters of furandicarboxylic acid have at least two of the properties.

5. A composition comprising a pentyl ester, which is the mixture according to claim 1.

6. A plasticizer or a plasticizer composition, comprising the mixture according to claim 1.

7. The plasticizer or the plasticizer composition according to claim 6, wherein the mixture comprises a dipentyl furan-2,5-dicarboxylate.

8. The plasticizer or the plasticizer composition according to claim 6, comprising at least two isomeric dipentyl furan-2,5-dicarboxylates.

9. The plasticizer or the plasticizer composition according to claim 8, wherein none of the at least two isomeric dipentyl furan-2,5-dicarboxylates has a proportion of more than 99.9% by weight in the ester mixture.

10. The plasticizer or the plasticizer composition according to claim 8, wherein the isomeric pentyl groups are selected from the group consisting of n-pentyl, 2-pentyl, 3-pentyl, 2-methylbutyl, 3-methylbutyl, 3-methylbut-2-yl, and 2-methylbut-2-yl.

11. The plasticizer composition according to claim 6, further comprising: a plasticizer selected from the group consisting of an alkyl benzoate, a dialkyl adipate, a glyceryl ester, a trialkyl citrate, an acylated trialkyl citrate, a trialkyl mellitate, a glycol dibenzoate, a dialkyl terephthalate, a dialkyl phthalate, a dialkanoyl ester of isosorbide, and a dialkyl ester of 1,2-, 1,3- or 1,4-cyclohexanedicarboxylic acid.

12. A process for preparing the mixture according to claim 1, comprising:
a) mixing a furandicarboxylic acid, a derivative thereof, or both with a mixture of isomeric pentanols, thereby obtaining a reaction mixture; and
b) heating the reaction mixture to a temperature of >50° C. and esterifying or transesterifying while removing at least one low molecular weight substance from the reaction mixture, thereby obtaining the mixture.

13. A process for preparing the mixture according to claim 1, comprising:
a) mixing 5-hydroxymethylfurfural, at least one furan derivative, or both with a mixture of isomeric pentanols, at least one catalyst, and at least one oxygen-comprising component, thereby obtaining a reaction mixture; and
b) adjusting the reaction mixture to a temperature of >0° C. and conducting an oxidative esterification, thereby obtaining the mixture.

14. A polymer composition comprising the mixture according to claim 1.

15. The polymer composition according to claim 14, further comprising: a polymer selected from the group consisting of polyvinyl chloride (PVC), polyvinylidene chloride (PVDC), a polyacrylate, a fluoropolymer, polyvinyl acetate (PVAc), polyvinyl alcohol (PVA), a polyvinyl acetal, a polystyrene polymer, a polyolefin, polyethylene-vinyl acetate (EVA), a polycarbonate, polyethylene terephthalate (PET), polybutylene terephthalate (PBT), polyoxymethylene (POM), polyamide (PA), polyethylene glycol (PEG), polyurethane (PU), a polysulphide (PSu), a biopolymer, polyhydroxybutyral (PHB), polyhydroxyvaleric acid (PHV), a polyester, starch, cellulose, a cellulose derivative, rubber, a silicone, and a mixture or a copolymer thereof.

16. The polymer composition according to claim 14, wherein the mixture is present in an amount of 5 to 200 parts by mass per 100 parts by mass of the polymer composition.

17. The polymer composition according to claim 14, further comprising: a copolymer of vinyl chloride with one or more monomers selected from the group consisting of vinylidene chloride, vinyl acetate, vinyl propionate, vinyl butyrate, vinyl benzoate, methyl acrylate, ethyl acrylate and butyl acrylate.

18. A moulding or a film comprising the polymer composition according claim 14.

19. The moulding or the film according to claim 18, wherein the film or moulding is a floor covering, a wall covering, a hose, a profile, a roofing sheet, a sealing sheet, a cable or wire sheath, a tarpaulin, an advertising banner, synthetic leather, packaging film, a medical article, a toy, a seal, or a furnishing article.

* * * * *